United States Patent [19]

Nylen et al.

[11] Patent Number: 4,783,264

[45] Date of Patent: Nov. 8, 1988

[54] PROCESS AND AN APPARATUS FOR THE RECOVERY OF A COMPOUND

[75] Inventors: Ulf T. G. Nylen; Bo G. Mattiasson, both of Lund, Sweden

[73] Assignee: Gambro Lundia AB, Sweden

[21] Appl. No.: 129,935

[22] Filed: Dec. 3, 1987

Related U.S. Application Data

[63] Continuation of Ser. No. 041,670, Apr. 21, 1987, abandoned, which is a continuation of Ser. No. 606,167, May 2, 1984, abandoned.

[30] Foreign Application Priority Data

May 9, 1983 [SE] Sweden ................. 8302638

[51] Int. Cl.$^4$ ............................................. B01D 13/00
[52] U.S. Cl. .................... 210/638; 210/639; 210/641; 210/651; 530/414
[58] Field of Search ............. 210/638, 639, 641, 648, 210/650, 651, 632; 530/414; 435/173, 180; 195/66

[56] References Cited

U.S. PATENT DOCUMENTS

| | | | |
|---|---|---|---|
| 3,850,798 | 11/1974 | Stoquist | 435/180 X |
| 4,039,413 | 8/1977 | Kraemer et al. | 435/173 X |
| 4,066,505 | 1/1978 | Schneider | 195/66 R |
| 4,361,484 | 11/1982 | Larsson et al. | 210/632 |
| 4,459,361 | 7/1984 | Gefter | 210/650 X |

FOREIGN PATENT DOCUMENTS 0046915 3/1982 European Pat. Off. .

*Primary Examiner*—Frank Sever
*Attorney, Agent, or Firm*—Lerner, David, Littenberg, Krumholz & Mentlik

[57] ABSTRACT

A process is disclosed for the recovery of a compound, for example, a peptide-containing compound, from a solution containing contaminants through combined affinity-chromatographic purification and ultrafiltration. The process comprises contacting the solution containing the compound and impurities with a first complex of ligand bound to a carrier so as to form a second complex of the compound, the ligand and the carrier, wherein the carrier is comprised of a macromolecular solid material; subsequently splitting off of the compound from the second complex to reform the compound and first complex; and separating of the compound from the first complex. An arrangement for the recovery of a compound from such a solution containing impurities is also disclosed.

16 Claims, 1 Drawing Sheet

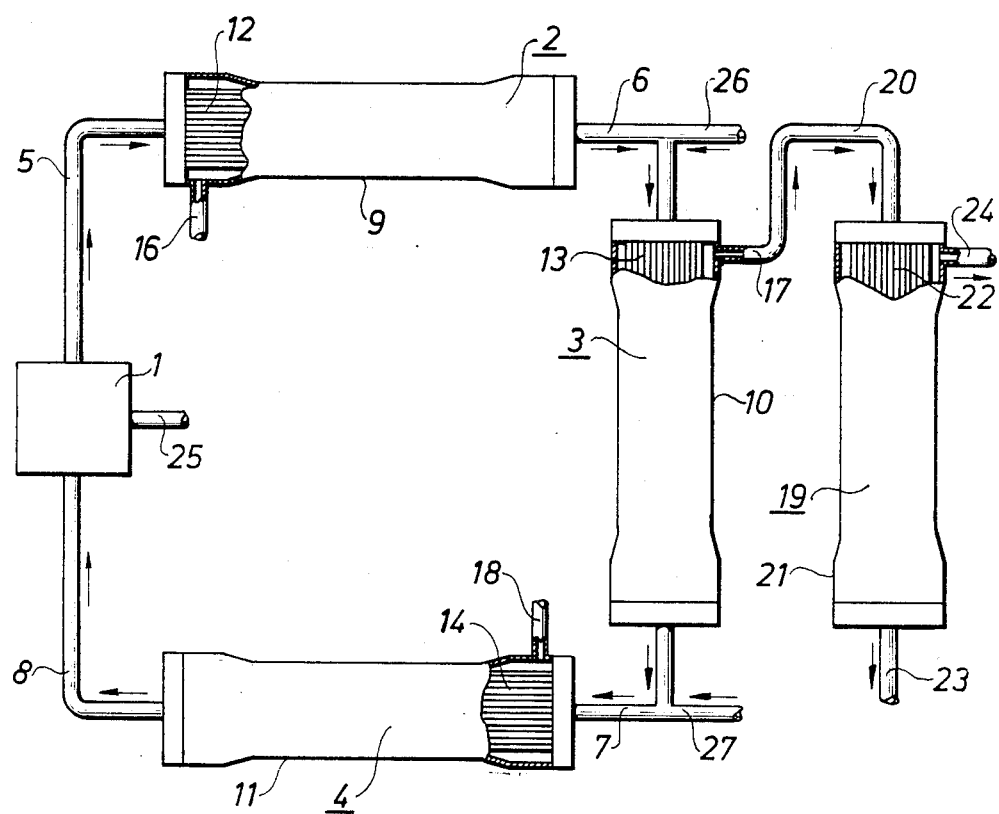

PROCESS AND AN APPARATUS FOR THE RECOVERY OF A COMPOUND

This is a continuation of application Ser. No. 041,670 filed Apr. 21, 1987, now abandoned, which was a continuation of Ser. No. 606,167, filed May 2, 1984, now abandoned.

BACKGROUND OF THE INVENTION

The present invention relates to a process and apparatus for the recovery of a compound, for example a peptide-containing compound, from a solution containing contaminants by combined affinity-chromatographic purification and ultrafiltration.

A process is described in published European patent application No. 0 046 915 which makes use of a carrier in dissolved form. A soluble complex of ligand and carrier is also disclosed in Schneider U.S. Pat. No. 4,066,505. However, because of the elongated molecular structure of the soluble carrier employed in such processes, it may slip through the pores of a membrane. Theoretically, this problem should be avoidable by using a membrane with a lower top cut-off limit, but in practice it is difficult to provide such a "tailor-made" membrane. Thus, the problem at the most can be reduced, but not totally and completely eliminated. In addition, a membrane which has such a lower top cut-off limit, i.e., within the interval appropriate in this particular context smaller than about $1 \times 10^6$ Dalton, requires a complicated technique of manufacture and is therefore considerably more expensive than the more readily accessible membranes with a top cut-off limit around $1 \times 10^6$ Dalton or over, e.g., up to $100 \times 10^6$ Dalton.

SUMMARY OF THE INVENTION

It has now been discovered that a process for recovering a compound, e.g., a peptide-containing compound, from a solution containing one or more other compounds of contaminating character can be provided which overcomes the disadvantages of the process employing soluble complex of ligand and carrier. In the process of the invention, the solution containing the compound and contaminants is contacted with a first complex of ligand bound to a carrier. The carrier is comprised of a macromolecular solid material, i.e., the ligand and attached carrier are insoluble in the solution. The first complex reacts with the compound in the mixing chamber to form a second complex comprising the compound, the ligand, and the carrier. The compound is then split off from the second complex to provide the compound and reformed first complex. The compound is separated from the first complex by using a semipermeable membrane which is permeable to the compound but impermeable to the first complex. Thus, the process of the invention utilizes the known technique of combined affinity-chromatographic purification and ultrafiltration, but also makes possible the use of the aforementioned less expensive membranes without any risk of leakage of the carrier used. This process can be used for the recovery of practically any type of compound from a solution containing other compounds of contaminating character, but it is particularly suitable for the recovery of, for example, enzymes, lectins, antibodies, antigens and haptens in pure form. Thus, although it is preferred to use the process and apparatus of the invention in connection with peptide-containing compounds, it can also be used for the recovery of other types of compounds other than those enumerated above including charged compounds of the ionic type.

The present invention also provides an arrangement for the recovery of a compound from a solution containing one or more other compounds of a contaminating character. This arrangement comprises a mixing chamber for contacting the desired compound in such solution with a first complex of ligand bound to a carrier so as to form a second complex of compound/ligand/carrier therein; a first membrane filter in fluid communication with the mixing chamber via a first duct, the first membrane filter being capable of filtering off the impurities from the second complex; and a second membrane filter in fluid communication with the first membrane filter via a second duct, the second membrane being capable of separating the compound from the first complex. This arrangement is particularly advantageous in carrying out the process of the invention as is more particularly discussed below.

The macromolecular solid material employed in accordance with the present invention, as distinguished from the elongated soluble carriers discussed above, has a more compact shape which through suitable dimensioning can be made sufficiently large in order to prevent passage through the pores of the membranes used. For example, membranes having a top cut-off limit around $1 \times 10^6$ Dalton or over, for example up to $100 \times 10^6$ Dalton, can be employed.

Examples of suitable solid macromolecular material for use as carrier in accordance with the invention are cells; agarose; starch; cellulose; chitin; gelatine; collagen; synthetic polymers of the latex or acrylic derivative type; and inorganic materials, for example, ceramic material, porous siliceous material, etc. Such solid material is used preferably in the form of spherical particles of a sufficiently large diameter so that they cannot penetrate through the pores of a membrane with a top cut-off limit of about $1 \times 10^6$ Dalton or over, for example up to about $100 \times 10^6$ Dalton. Examples of such diameters are over about 0.1 microns, such as between about 1 and about 50 microns, preferably between about 2 and about 10 microns.

Examples of suitable ligands which can be bound to the macromolecular solid material for use in the process of the invention include inhibitors, carbohydrate structures, antigens, antibodies, haptens, complement factors (e.g., C1Q), cofactors, enzymes, nucleic acids, conglutinin and surface receptors, for example bacterial, such as protein A and protein G. The ligand employed depends upon the type of peptide-containing compound which is to be recovered. One important demand which is made on the ligand is that it ought to be able to bind with biospecific affinity to the desired compound to be recovered.

The expression "bound to the solid macromolecular material" refers to any suitable type of binding, e.g., physical or chemical binding. Moreover, it also includes such cases where the ligand is naturally occurring on the solid material, e.g., surface structures on killed microbial cells, for example, yeast cells.

In accordance with the invention, it is appropriate to separate the impurities before the second complex is split to reform the compound and the first complex. Preferably, this separation of the impurities from the solution containing the second complex, e.g., carrier/ligand/peptide-containing compound, is performed by using a semipermeable membrane which is permeable to the impurities but impermeable to the second complex. Examples of suitable membranes for this purification step include those which have a cut-off of between about 50,000 and about $100 \times 10^6$ Dalton, where the lower limit, of course, can be higher depending on the size of the impurities. Generally, it can be said that the impurities will be separated more rapidly with a higher bottom cut-off limit.

In the process of the invention, the compound may be split off from the second complex formed in any appropriate manner. It may be achieved, for example, through modification of the pH of the solution containing the second complex by the addition thereto, e.g., of an acid, or through modification of the ionic strength of the solution by the addition, for example, of a salt solution. The splitting off can also be achieved through the addition of a ligand present in free form (i.e., not attached or bound to the carrier) in a sufficient concentration to drive out the ligand bound to the carrier and thus break the bond between this first complex and the peptide-containing compound. The choice of a suitable free ligand is determined in each individual case by the type of compound which is to be recovered, while it is a general rule that the ligand chosen should be able to bind to this compound. Examples of suitable free ligands which can be used are low-molecular sugars, e.g., mono and disaccharides, in the purification of lectins, and antigens or parts thereof in the purification of antibodies.

The compound can be separated from the dissociating agent, e.g., the ligand added in free form, by the use of a semipermeable membrane which is permeable to the dissociating agent but impermeable to the compound or vice versa. Typically, the membrane has a sufficiently low top cut-off limit to prevent penetration by the compound but has a sufficiently high top cut-off limit to allow passage of the free ligand, as will be explained further below. A semipermeable membrane with a top cut-off limit below about 35,000 Dalton may be appropriate.

The solution containing the first complex of carrier with bound ligand reformed after the splitting off of the compound is preferably reused for contact with more of the original solution containing the desired compound as well as impurities. As a result, a substantially closed circuit for the carrier with bound ligand is created. In certain cases, it can be appropriate to add a buffer or the like for the reconditioning (pH-adjustment) of the solution containing the first complex of carrier with bound ligand prior to its reuse.

BRIEF DESCRIPTION OF THE DRAWING

The invention will be described in more detail in the following with reference to the attached drawing which shows schematically an apparatus for the recovery of a compound from a solution in accordance with one embodiment of the invention.

DETAILED DESCRIPTION OF THE DRAWING

In the embodiment shown in the drawing by way of example, a substantially closed system for the first complex of ligand bound to a carrier is used. The system comprises in turn an appropriately designed mixing chamber 1, a first membrane filter 2, a second membrane filter 3, and a third membrane filter 4 connected with one another by means of ducts 5, 6, 7, and 8, respectively, as shown in the figure.

The membrane filters 2, 3, and 4 are constituted preferably of semipermeable hollow fibers 12, 13, and 14, respectively, with their respective axial fiber hollows adapted to form flow ducts for the complexes including the ligand bound in the carrier in the closed system, as will be described. Moreover, the membrane filters comprise outlets 16, 17, and 18, respectively, for the filtrate including matters which can penetrate the pores in the respective hollow fiber walls.

The first membrane filter 2 thus comprises semipermeable hollow fibers 12 in a housing 9 with the axial fiber hollows in connection with the ducts 5 and 6. Moreover, the membrane filter 2 comprises an outlet 16 for the impurities filtered off.

The second membrane filter 3, too, comprises preferably semipermeable hollow fibers 13 in a housing 10 with the axial fiber hollows in connection with the ducts 6 and 7. Moreover, the membrane filter comprises an outlet 17 for the compound to be separated.

The third membrane filter 4 comprises preferably semipermeable hollow fibers 14 in a housing 11 in connection with the ducts 7 and 8. Moreover, this third membrane filter comprises an outlet 18 for the salts or the like filtered off.

As can be seen in the figure, the arrangement may also comprise a fourth membrane filter 19 in connection with the outlet 17 on the second membrane filter 3 via a duct 20. This fourth membrane filter comprises a housing 21 with semipermeable hollow fibers 22 arranged inside the housing, the axial fiber hollows being connected to the duct 20, and an outlet 23 for the purified compound. Moreover, the four membrane filter 19 comprises an outlet 24, e.g., for free ligand filtered off, as will be described in the following.

Finally, the arrangement can comprise a duct 25 in connection with the mixing chamber 1 for introducing solution containing the peptide-containing compound together with impurities; a duct 26 in connection with the duct 6 for feeding dissociation agent, e.g., competing free ligand, an acid solution or a salt solution; and a duct 27 in connection with the duct 7 for feeding, for example, the buffer for reconditioning the ligand bound to the carrier.

The process in accordance with the invention can be performed in the following manner with the help of the apparatus shown.

The solution containing the desired compound, e.g., a peptide-containing compound, together with impurities is introduced into the mixing chamber 1 via the duct 25 from a source for this solution, not shown on the drawing. In the mixing chamber 1 the solution is brought into contact with the first complex of ligand bound to the carrier, which first complex is circulating in the closed system described above. A second complex consisting of carrier/ligand/peptide-containing compound is formed. From the mixing chamber 1 the solution containing the second complex formed, together with the impurities, is pumped into the first membrane filter 2 via the duct 5. In the first membrane filter 2 the impurities are filtered out through the pores in the semipermeable hollow fibers 12 and are discharged via the outlet 16. The solution containing the second complex so purified is pumped from the first membrane filter 2 into the second membrane filter 3 via the duct 6. Dissociating agent is introduced into the duct 6 via the duct 26, which dissociating agent splits the peptide-containing compound off of the second complex to reform the peptide-containing compound and the first complex. In the second membrane filter 3 a filtering off of the peptide-containing compound thus split off, together with dissociating agent, takes place through the pores in the semipermeable hollow fibers 13 and duct 17. The solution containing the reformed first complex of ligand bound to the carrier is pumped from the second membrane filter 3 into the third membrane filter 4 via the duct 7. A buffer solution is fed via the duct 27 in connection with duct 7. From the third membrane filter 4 the reformed first complex of ligand bound to the carrier is then pumped into the mixing chamber 1 via the duct 8 for reuse. Any residues of dissociating agent or salts remaining are filtered off from the solution containing the first complex through the pores in the semipermeable hollow fibers 14 and discharged via the outlet 18.

The pepetide-containing compound separated in the second membrane filter 3 together with any dissociating agent is withdrawn via the outlet 17 and introduced into the fourth membrane filter 19 via the duct 20 for separation of the dissociating agent which is filtered through the pores in the semipermeable hollow fibers 22 and withdrawn through the outlet 24. The purified peptide-containing compound is withdrawn through the outlet 23.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A process for separating a peptide-containing compound from one or more contaminants, the process comprising the steps of:
    (a) forming a liquid mixture including said peptide-containing compound in solution and also including a first complex of a ligand on an insoluble solid particulate carrier so as to form in said mixture a second complex of said ligand, said peptide-containing compound and said particulate carrier;
    (b) contacting said mixture containing said second complex with a first semi-permeable membrane having a top cutoff of about $1 \times 10^6$ Daltons or over permeable to said contaminants but impermeable to said particulate carrier so as to separate said contaminants from said mixture, said carrier precluding said second complex, and hence said peptide-containing compound, from passing through the pores of said first semi-permeable membrane;
    (c) splitting off said peptide-containing compound from said second complex so as to provide a second liquid mixture including reformed first complex and said peptide-containing compound solution; and
    (d) contacting said second liquid mixture with a second semi-permeable membrane permeable to said peptide-containing compound but impermeable to said particulate carrier so as to separate said peptide-containing compound from the reformed first complex, leaving a third liquid mixture containing said reformed first complex.

2. A process according to claim 1, wherein said solid particulate carrier is selected from the group consisting of cells, agarose, starch, cellulose, chitin, gelatine, collagen, synthetic latex polymers, synthetic acrylic polymers, and inorganic materials.

3. A process according to claim 1, wherein said solid particulate carrier comprises particles having a size greater than about 0.1 microns.

4. A process according to claim 1, wherein said solid particulate carrier comprises particles of from about 1 to about 50 microns in size.

5. A process according to claim 1 wherein said solid particulate carrier comprises particles of from about 2 to about 10 microns in size.

6. A process according to claim 1, wherein said ligand is selected from the group consisting of inhibitors, carbohydrate structures, antigens, antibodies, haptens, cofactors, C1Q, enzymes, nucleic acids, conglutinin and surface receptors.

7. A process according to claim 6, wherein the ligand is selected from protein A or protein G.

8. A process according to claim 1, wherein said step of splitting off said peptide-containing compound from said second complex comprises the addition of a dissociating agent selected from the group consisting of an acid solution, a salt solution or a ligand present in free form which is capable of binding to the peptide-containing compound with simultaneous splitting off of the compound from said second complex whereby said step of contacting said second liquid mixture with said second semi-permeable membrane yields said separated peptide-containing compound in a solution with said dissociating agent.

9. A process according to claim 8, wherein the ligand present in free form is selected from the group consisting of low-molecular sugars and antigens or parts thereof.

10. A process according to claim 8, including contacting said solution containing said peptide-containing compound and said dissociating agent with a third semi-permeable membrane so as to separate said peptide-containing compound from said dissociating agent.

11. A process according to claim 10, wherein said dissociating agent comprises said ligand present in free form, and wherein said third semi-permeable membrane is permeable to said ligand in free form but impermeable to said peptide-containing compound.

12. A process according to claim 10, wherein said dissociating agent comprises said ligand in free form, and wherein said third semi-permeable membrane is permeable to said peptide-containing compound but impermeable to said ligand in free form.

13. A process according to claim 8, including recycling said first complex for further contact with a solution containing the peptide-containing compound.

14. A process according to claim 13, including reconditioning said first complex for such recycle by the addition of a suitable buffer solution.

15. A process as claimed in claim 1 further comprising the step of transferring said mixtures between said steps by continuously circulating said mixtures along a closed circuit of ducts, said first and second semipermeable membranes being disposed along said closed circuit.

16. A process as claimed in claim 1 further comprising the step of passing said third liquid mixture containing said reformed first complex back to step (a).

* * * * *